United States Patent
Helmer

(10) Patent No.: US 10,610,645 B2
(45) Date of Patent: Apr. 7, 2020

(54) ACTIVATING MECHANISM FOR A MEDICAMENT DELIVERY DEVICE AND MEDICAMENT DELIVERY DEVICE

(71) Applicant: Sanofi, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 702 days.

(21) Appl. No.: 15/309,737

(22) PCT Filed: May 11, 2015

(86) PCT No.: PCT/EP2015/060289
§ 371 (c)(1),
(2) Date: Nov. 8, 2016

(87) PCT Pub. No.: WO2015/173167
PCT Pub. Date: Nov. 19, 2015

(65) Prior Publication Data
US 2017/0143903 A1    May 25, 2017

(30) Foreign Application Priority Data

May 12, 2014  (EP) .................................. 14305686

(51) Int. Cl.
*A61M 5/24* (2006.01)
*A61M 5/32* (2006.01)
*A61M 5/20* (2006.01)

(52) U.S. Cl.
CPC ............ *A61M 5/24* (2013.01); *A61M 5/2466* (2013.01); *A61M 5/3202* (2013.01);
(Continued)

(58) Field of Classification Search
CPC .... A61M 5/24; A61M 5/3287; A61M 5/2466; A61M 5/3202; A61M 2005/247
See application file for complete search history.

(56) References Cited

U.S. PATENT DOCUMENTS

| 3,820,652 A | 6/1974 | Thackston |
| 4,303,069 A | 12/1981 | Cohen |

(Continued)

FOREIGN PATENT DOCUMENTS

| DE | 2056688 | 3/1972 |
| JP | 2014-500089 | 1/2014 |

(Continued)

OTHER PUBLICATIONS

International Search Report and Written Opinion in International Application No. PCT/EP2015/060289, dated Aug. 17, 2015, 10 pages.

(Continued)

*Primary Examiner* — Bradley J Osinski
(74) *Attorney, Agent, or Firm* — Fish & Richardson P.C.

(57) ABSTRACT

The disclosure relates to an activating mechanism for a medicament delivery device, wherein the activating mechanism includes a cartridge containing a dosage of a medicament, a cartridge carrier holding the cartridge and comprising a distal carrier section, a hollow injection needle arranged within a distal end of the cartridge carrier comprising an inner needle section targeted inside the cartridge carrier, whereby the inner needle section is spaced from the cartridge in a distal direction (D) when the medicament delivery device is in an initial position (P1), a removable needle cap to cover and seal an outer needle section of the injection needle that is targeted outside the cartridge carrier.

20 Claims, 3 Drawing Sheets

(52) U.S. Cl.
CPC ..... *A61M 5/3287* (2013.01); *A61M 2005/206* (2013.01); *A61M 2005/2013* (2013.01); *A61M 2005/247* (2013.01)

(56) References Cited

U.S. PATENT DOCUMENTS

| | | |
|---|---|---|
| 4,957,490 A | 9/1990 | Byrne et al. |
| 2012/0179109 A1 | 7/2012 | Takemoto et al. |

FOREIGN PATENT DOCUMENTS

| | | |
|---|---|---|
| WO | WO 2012/073032 | 6/2012 |
| WO | WO 2011/108575 | 6/2013 |
| WO | WO 2015/173167 | 11/2015 |

OTHER PUBLICATIONS

International Preliminary Report on Patentability in International Application No. PCT/EP2015/060289, dated Nov. 16, 2016, 7 pages.

ACTIVATING MECHANISM FOR A MEDICAMENT DELIVERY DEVICE AND
MEDICAMENT DELIVERY DEVICE

CROSS-REFERENCE TO RELATED APPLICATIONS

This application is a U.S. national stage application under 35 USC § 371 of International Application No. PCT/EP2015/060289, filed on May 11, 2015, which claims priority to European Patent Application No. 14305686.9 filed on May 12, 2014, the entire contents of which are incorporated herein by reference.

TECHNICAL FIELD

The disclosure relates to an activating mechanism for a medicament delivery device and a medicament delivery device incorporating such an activating mechanism.

BACKGROUND

Administering an injection is a process which presents a number of risks and challenges for users and healthcare professionals, both mental and physical. Pre-filled syringes containing a selected dosage of a medicament for administering the medicament to a patient are known in the art. The cartridges may be stored in a blistered package so that they keep sterile until the time of use.

There remains a need for an improved activating mechanism for a medicament delivery device and an improved medicament delivery device incorporating such an activating mechanism.

SUMMARY

It is an object of the present invention to provide an improved activating mechanism for a medicament delivery device and an improved medicament delivery device comprising such a activating mechanism.

The object is achieved by an activating mechanism according to claim 1 and by a medicament delivery device according to claim 12.

Exemplary embodiments are given in the dependent claims.

According to the present disclosure, there is provided an activating mechanism for a medicament delivery device, wherein the activating mechanism comprises a cartridge containing a dosage of a medicament, a cartridge carrier holding the cartridge and comprising a distal carrier section and a hollow injection needle, in particular a double ended needle, that is arranged within a distal end of the cartridge carrier. The injection needle comprises an inner needle section that is targeted inside the cartridge carrier, whereby the inner needle section is spaced from the cartridge in a distal direction when the medicament delivery device is in an initial position. The activating mechanism further comprises a removable needle cap to cover and to seal an outer needle section of the injection needle that is targeted outside the cartridge carrier, wherein at least the distal carrier section is made from a resilient material so that the distal carrier section is allowed to deform radially outwards when the needle cap is removed and the cartridge is moved in the distal direction.

The provided activating mechanism for the medicament delivery device enables an unsealing of a non-blistered sterile packed cartridge with the injection needle pre-assembled on the cartridge carrier. The initial position of the medicament delivery device is a position in which the medicament delivery device would be presented to a user prior to use, wherein the injection needle and the cartridge are sealed against environmental influences. In the operating position, the injection needle is in fluid communication with the medicament stored in the cartridge. The resilient design of the cartridge carrier allows a release of the cartridge that is engaged with the cartridge carrier including injection needle.

In an exemplary embodiment, the distal carrier section comprises a carrier collar that protrudes in a radial inward direction as well as in a radial outward direction, wherein the carrier collar is provided to retain the cartridge in position as long as the medicament delivery device is in the initial position. Instead of the carrier collar, there may be arranged a number of resilient arms that protrudes in the radial inward direction and that are adapted to retain the cartridge in position when the medicament delivery device is in the initial position.

The activating mechanism further comprises a piston rod that is adapted to engage with a bung for displacing the bung within the cartridge. The bung limits the cavity of the cartridge proximally. Due to the displacement of the bung, the medicament stored in the cartridge is ejected through the injection needle into an injection site, e.g. a patient's skin. By applying a force on the piston rod engaged with the bung, the cartridge will be moved in the distal direction, whereby the distal carrier section and the carrier collar are deformed radially outwards. The piston rod may be connected to a button for automatic medicament delivery or may be applied with a manual force In an exemplary embodiment, the piston rod comprises a rod tip on a distal end that is adapted to engage into a correspondingly formed bung notch. Thus, the rod tip and the bung notch build a positive locking fit for a reliable mechanical engagement between the piston rod and the bung.

To secure a sealing of the inner needle section against environmental influences in the initial position the cartridge carrier comprises a carrier sealing foil, whereby in an exemplary embodiment, the piston rod is spaced from the carrier sealing foil when the medicament delivery device is in the initial position. The carrier sealing foil may be pierced by the rod tip of the piston rod.

In an exemplary embodiment, the carrier sealing foil is arranged across an open proximal end, thus securing the sealing of the inner needle section before the beginning of an injection process. In an alternate embodiment, the sealing foil may be arranged closer to the injection needle in a manner such that the cartridge is outside a sealing area of the sealing foil. In this case, the cartridge may comprise a piercing adapter that is arranged on a flange of the cartridge. The piercing adapter replaces the piercing function of the piston rod. In a further alternate embodiment, the carrier sealing foil is designed as a piercable sealing membrane that is arranged within a cork, whereby the cork limits the proximal end of the cartridge carrier. This would simplify a final assembly step regarding to arrange a carrier sealing foil.

In an exemplary embodiment, an inner diameter of the carrier collar is smaller than a maximum outer diameter of the cartridge, wherein the carrier collar engages a cartridge shoulder for restricting movement of the cartridge in the distal direction relative to the cartridge carrier when the medicament delivery device is in the initial position. The carrier collar retains the cartridge in position before the injection process started so that it remains sealed until the injection process starts.

On the other hand, the resilient carrier collar is retained in position by the removable needle cap, whereby a proximal inner surface of the needle cap fits closely to an outer surface of the distal carrier section when the medicament delivery device is in the initial position in order to restrict a radial outward deformation of the distal carrier section. By removing the needle cap, the distal carrier section is allowed to deform radially outwards due to a distal movement of the cartridge.

In a further exemplary embodiment, a wall thickness of the distal carrier section is reduced compared to a wall thickness of the remaining cartridge carrier with exception of the carrier collar. The reduced wall thickness of the distal carrier section allows an easier deformation of this part of the cartridge carrier compared with the remaining cartridge carrier. Thus, the cartridge is released and still guided by the remaining cartridge carrier at the same time.

The needle cap may comprise a first gap enclosing the outer needle section in the initial position, wherein a radial outer surface of a carrier projection, associated with a distal end of the cartridge carrier and protruding axially in the distal direction, is enclosed at least distally by a proximal radial surface of the first gap. Consequently, the outer needle section is completely enclosed by the needle cap and the carrier projection so that the outer needle section is sealed against environmental influences until the needle cap is removed.

In an exemplary embodiment, the activating mechanism may further comprise a sleeve that is movable along a longitudinal axis in a proximal and/or a distal direction so as to expose or to cover the outer needle section. The covering of the outer needle section prevents a user from touching and seeing the injection needle so that the user is protected.

Furthermore, there is provided a medicament delivery device comprising the activating mechanism as it is described before. The medicament delivery device is suitable for use with a manual needle insertion and a manual medicament delivery as well as for use with an automatic needle insertion and/or an automatic medicament delivery. Particularly, the medicament delivery device is suitable for use in autoinjectors that are sleeve- or button triggered.

Further scope of applicability of the present disclosure will become apparent from the detailed description given hereinafter. However, it should be understood that the detailed description and specific examples, while indicating exemplary embodiments, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

In the present application, when the term "proximal section/end" is used, this refers to the section/end of the medicament delivery device, or the sections/ends of the components thereof, which under use of the medicament delivery device is located the furthest away from the medicament delivery site of the patient. Correspondingly, when the term "distal section/end" is used, this refers to the section/end of the medicament delivery device, or the sections/ends of the components thereof, which under use of the medicament delivery device is located closest to the medicament delivery site of the patient.

Figure 1:
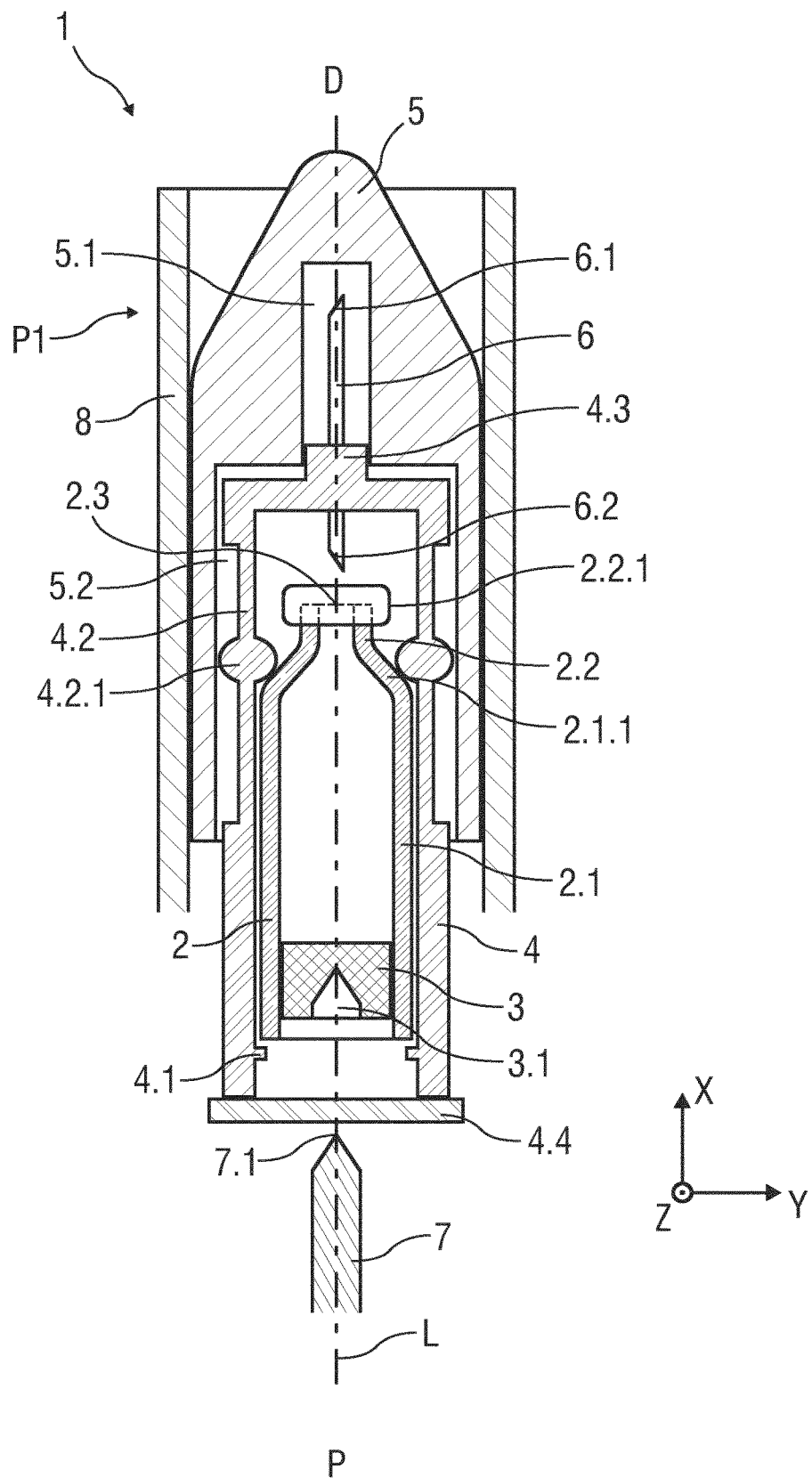
FIG. 1 is a schematic longitudinal section view of an exemplary embodiment of a medicament delivery device in an initial position.
Figure 2:
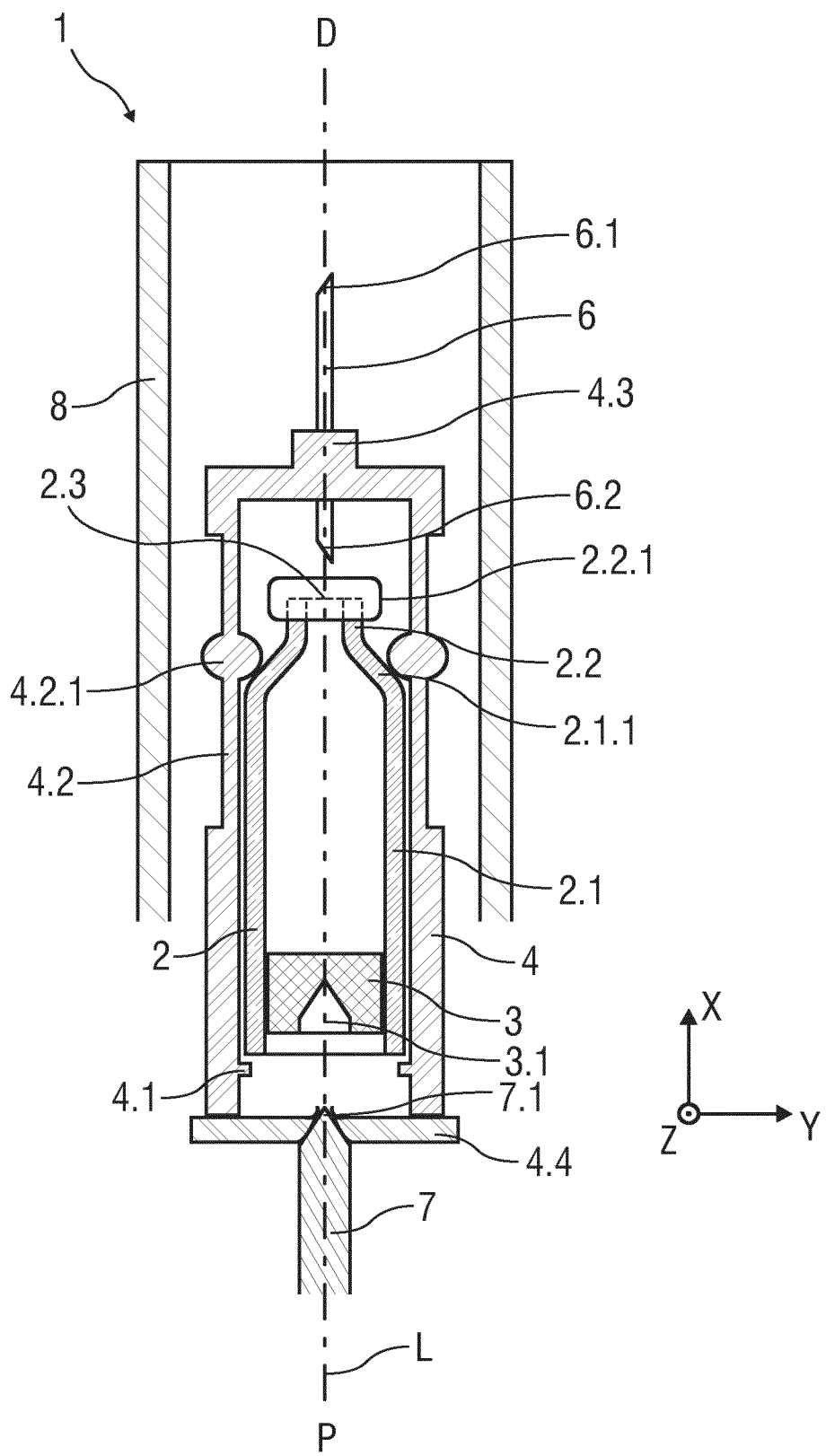
FIG. 2 is a schematic longitudinal section view of an exemplary embodiment of a medicament delivery device between the initial position and an operating position.
Figure 3:
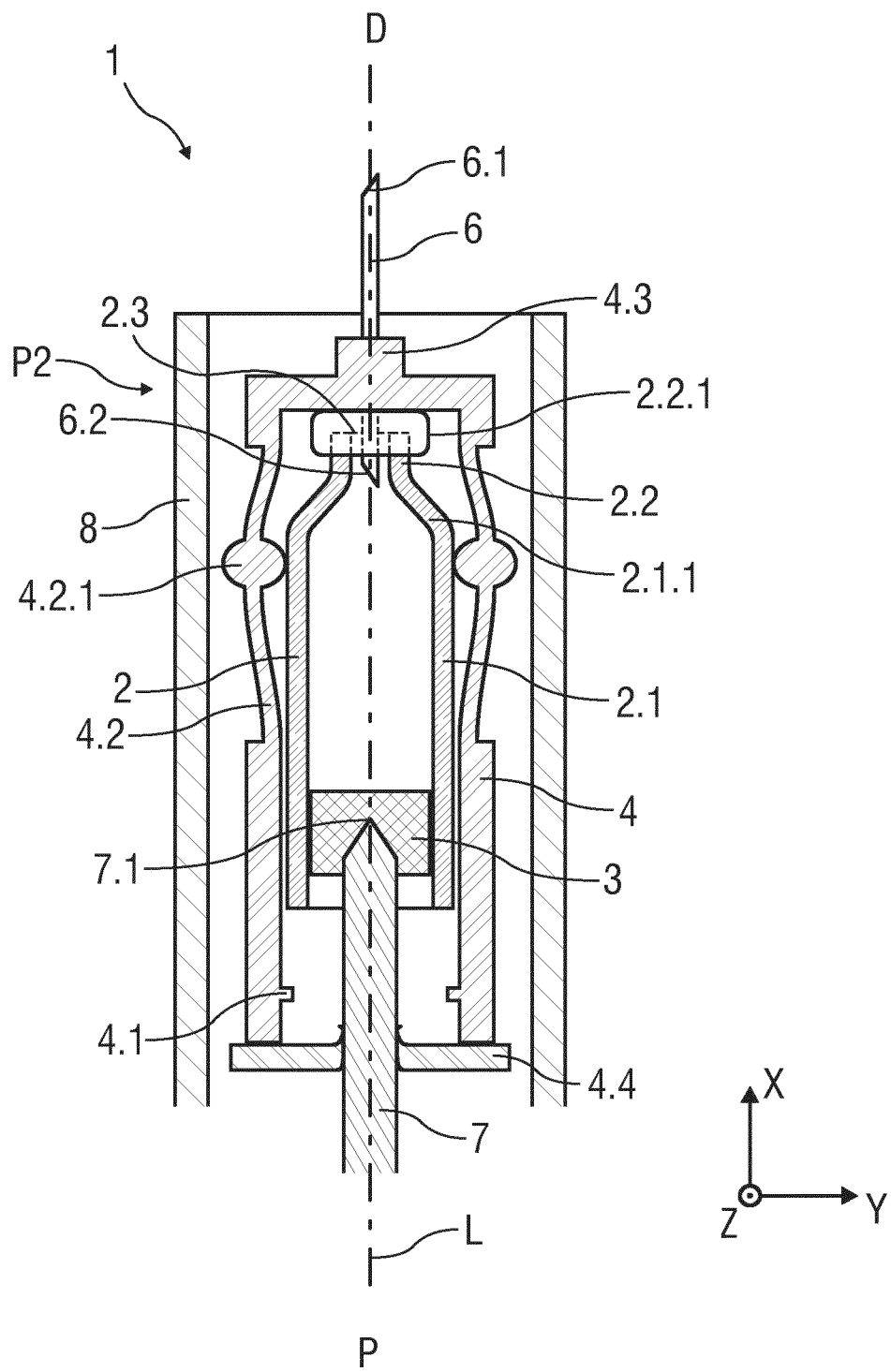
FIG. 3 is a schematic longitudinal section view of an exemplary embodiment of a medicament delivery device in the operating position.

By way of illustration, a cartesian coordinate system with the coordinates x, y and z is illustrated in all FIGS. 1 to 3.

FIG. 1 shows a schematic longitudinal section view of an exemplary embodiment of a medicament delivery device 1, whereby the medicament delivery device 1 is in an initial position P1.

In context of the present application, the initial position P1 of the medicament delivery device 1 is a position in which the medicament delivery device 1 would be presented to the user prior to use before starting an injection process.

The medicament delivery device 1 comprises a cartridge 2 forming a cavity that contains a dosage of a medicament. The cartridge 2 comprises a cylindrically shaped main body section 2.1 and a neck section 2.2. The neck section 2.2 is arranged on a distal end of the main body section 2.1 and comprises a cartridge flange 2.2.1.

A cartridge shoulder 2.1.1 narrowing towards the neck section 2.2 connects the main body section 2.1 with the neck section 2.2. A cap is provided across the cartridge flange 2.2.1 to retain a cartridge sealing element 2.3, e. g. a fluid impermeable membrane or foil, that is arranged across an open end of the neck section 2.2. Furthermore, a bung 3 is disposed within the cartridge 2 on a proximal end of the main body portion 2.1 when the medicament delivery device 1 is in the initial position P1. The bung 3 limits the cavity of the cartridge 2 in a proximal direction P and comprises a distal face and a proximal face.

The cartridge 2 is held in a substantially cylindrical shaped and hollow cartridge carrier 4 that comprises a circumferential carrier rib 4.1. The carrier rib 4.1 is arranged proximally on an inner surface and protrudes in a radial inward direction in a manner to engage the cartridge 2 for restricting movement along a longitudinal axis L in a proximal direction P relative to the cartridge carrier 4. Alternatively, more than one carrier rib 4.1 may be arranged along the circumference of the inner radial surface of the cartridge carrier 4 with a uniform or non-uniform distribution.

Furthermore, the cartridge carrier 4 comprises a distal carrier section 4.2 with a reduced circumferential wall thickness regarding an outer radial surface. In particular, an outer diameter of the distal carrier section 4.2 is smaller than an outer diameter of the remaining cartridge carrier 4, whereas an inner diameter of the distal carrier section 4.2 corresponds with an inner diameter of the remaining cartridge carrier 4.

The distal carrier section 4.2 comprises a carrier collar 4.2.1 that protrudes in a radial outward direction as well as in a radial inward direction. In particular, an outer diameter of the carrier collar 4.2.1 corresponds with the outer diameter of the remaining cartridge carrier 4, in example a maximum outer diameter of the cartridge carrier 4, and an inner diameter of the carrier collar 4.2.1 is smaller than an inner diameter of the cartridge carrier 4. The distal collar 4.2.1 is arranged completely around the circumference of the distal carrier section 4.2.

The carrier collar 4.2.1 is provided to support the cartridge shoulder 2.1.1 of the cartridge 2 such that the cartridge 2 is prevented from moving along the longitudinal axis L in a distal direction D relative to the cartridge carrier 4. Alternatively, instead of a distal collar 4.2.1 there may be provided a number of resilient arms that are arranged around the circumference of the distal carrier section 4.2 spaced apart from each other in a circumferential direction.

At least the distal carrier section 4.2 is made from a resilient material, in particular an optically transparent plastic like polypropylene or polyethylene, by which the distal carrier section 4.2 is allowed to be deformed radially outwards. Thus, the cartridge 2 is further movable into the distal direction D until the distal end of the cartridge flange 2.2.1 abuts against an inner bottom surface of the distal end of the cartridge carrier 4 as it is shown in FIG. 3. Alternatively, the whole cartridge carrier 4 may be made from a resilient material.

To ensure a distal sealing of the cartridge 2 in the initial position P1, the distal carrier section 4.2 is prevented from deforming radially outwards by a removable needle cap 5 that is fitted over a hollow injection needle 6 when the medicament delivery device 1 is in the initial position P1.

The needle cap 5 covers and seals an outer needle section 6.1 of an injection needle 6 that is targeted outside the cartridge carrier 4. The injection needle 6 is received within the cartridge carrier 4 in a manner such that the injection needle 6 is arranged throughout a distal end of the cartridge carrier 4, whereby the distal end of the cartridge carrier 4 comprises a carrier projection 4.3 directed towards the distal direction D with an opening for receiving the injection needle 6. An inner needle section 6.2 is targeted inside the cartridge carrier 4.

When the medicament delivery device 1 is in the initial position P1, the inner needle section 6.2 is distally spaced from the distal end of the cartridge 2. The inner needle section 6.2 is sealed against environmental influences by a carrier sealing foil 4.4 that is arranged across an open proximal end of the cartridge carrier 4. The carrier sealing foil 4.4 may be designed as a fluid impermeable membrane equal to the cartridge sealing element 2.3 or as an alternative compliant foil or membrane. Furthermore, the carrier sealing foil 4.4 may be designed as a piercable sealing membrane that is arranged within a cork that limits the proximal end of the cartridge carrier 4.

For sealing the outer needle section 6.1 the inside dimensions of the needle cap 5 are designed corresponding to dimensions of the outer needle section 6.1 and dimensions of the distal end and the distal carrier section 4.2 of the cartridge carrier 4. For this purpose, the needle cap 5 comprises a first gap 5.1 and a second gap 5.2, whereby the first gap 5.1 encloses the outer needle section 6.1. A proximal radial surface of the first gap 5.1 is applied directly against a radial outer surface of the carrier projection 4.3 such that the outer needle section 6.1 is completely enclosed and thus, sealed. The second gap 5.2 fits directly to the first gap 5.1 in the proximal direction P. The second gap 5.2 corresponds with the maximum outer diameter of the cartridge carrier 4 so that a radial surface of the second gap 5.2 fits closely to an outer radial surface of the cartridge carrier 4 regarding the maximum outer diameter of the cartridge carrier 4.

The medicament delivery device 1 furthermore comprises a piston rod 7 that is arranged to engage the bung 3 for displacing it within the cartridge 2 during use of the medicament delivery device 1. Therefore, the bung 3 comprises a bung notch 3.1 arranged within the proximal face and corresponding with a rod tip 7.1 of the piston rod 7 targeted in the distal direction D for realizing a positive-locking fit between the piston rod 7 and the bung 3.

As long as the medicament delivery device 1 is in the initial position P1, the piston rod 7 is spaced from the bung 3 in the proximal direction P. The piston rod 7 may be attached to a not shown body or housing. In one exemplary embodiment the piston rod 7 may be integrally shaped with the body or housing. In another exemplary embodiment the piston rod 7 may be secured to the body or housing, e.g., by latches.

Moreover, the medicament delivery device 1 comprises a sleeve 8 adapted to center the cartridge 2 and the cartridge carrier 4 within the sleeve 8 and to cover the injection needle 6 preventing a user from touching and seeing it when the medicament delivery device 1 is in the initial position P1. The sleeve 8 may be slidably coupled to the body or housing for allowing relative movement in the distal direction D and/or in the proximal direction P.

FIG. 2 shows a schematic longitudinal section view of an exemplary embodiment of the medicament delivery device 1 that is between the initial position P1 and an operating position P2 shown in FIG. 3. The needle cap 5 has been removed and the piston rod 7 has moved in the distal direction D relative to the cartridge carrier 4 in a manner such that the carrier sealing foil 4.4 is pierced by the rod tip 7.1 of the piston rod 7. The cartridge 2 is still held in position as shown in FIG. 1.

In a not shown alternative embodiment, the sealing foil 4.4 is arranged distally spaced from the cartridge 2, whereby the cartridge 2 is provided with a piercing adapter that is arranged on the flange 2.2.1 of the cartridge 2. The piercing adapter replaces the piercing function of the piston rod 7.

Due to an engagement of the piston rod 7 and the bung 3 and an applied force on the piston rod 7 in the distal direction D, the cartridge 2 moves in the distal direction D until the cartridge flange 2.2.1 abuts against an inner bottom surface of the distal end of the cartridge carrier 4 as it is shown in FIG. 3.

FIG. 3 shows a schematic longitudinal section view of an exemplary embodiment of the medicament delivery device 1 in the operating position P2 at the beginning of an injection process.

The cartridge flange 2.2.1 abuts against the inner bottom surface of the distal end of the cartridge carrier 4. Due to the movement of the cartridge 2 the resilient distal carrier section 4.2 comprising the carrier collar 4.2.1 is deformed in the radial outward direction such that the distal section's 4.2 cross section is no longer circular. The force required for deforming the distal carrier section 4.2 is defined by the resilience of the material and by the geometry of the distal carrier section 4.2.

The inner needle section 6.2 has pierced the cartridge sealing element 2.3 and thus is in fluid communication with the medicament stored in the cartridge 2.

To start the ejection of the medicament into the injection site, the piston rod 7 has to displace the bung 3 within the cartridge 2 by applying a force on the piston rod 7 in the distal direction D.

In context of the present application the medicament delivery device 1 can be used as a manual device with a manual needle insertion and a manual medicament delivery. Likewise, the medicament delivery device 1 is suitable for use as an auto-injector with automatic needle insertion and/or automatic medicament delivery in order to adjust the injection force. Particularly, the medicament delivery device 1 is suitable for use in autoinjectors that are sleeve- or button triggered.

In order to perform the injection process, the medicament delivery device 1 may be operated according to the following exemplary method.

The needle cap 5 is removed from the medicament delivery device 1.

By applying a force on the piston rod 7 in the distal direction D, the piston rod 7 moves into the distal direction D until the rod tip 7.1 engages with the bung notch 3.1, whereby the carrier sealing foil 4.4 is pierced by the rod tip 7.1 as it is shown in FIG. 2.

Moving the piston rod 7 further into the distal direction D causes a distal movement of the cartridge 2, because the force required moving the cartridge 2 in the distal direction D is smaller than the force required moving the bung 3 within the cartridge 2 in the distal direction D.

Due to the distal movement of the cartridge 2, the distal section 4.2 deforms radially outwards, thus increasing the inner diameter of the cartridge carrier 4. The cartridge 2 passes the carrier collar 4.2.1 and moves distally until the cartridge flange 2.2.1 abuts against the inner bottom surface of the cartridge carrier 4. At the same time, the injection needle 6 pierces the cartridge sealing element 2.3, thus getting in fluid communication with the medicament stored in the cartridge 2.

Now, the force required to displace the bung 3 within the cartridge 2 into the distal direction D is smaller than the force required moving the cartridge 2 into the distal direction D. Due to the distal movement of the bung 3 with respect to the cartridge 2, the medicament is ejected through the injection needle 6 into the injection site. The ejection of the medicament stops when the distal face of the bung 3 abuts against the cartridge shoulder 2.1.1 inside the cartridge 2. After that, the medicament delivery device 1 may be removed from the injection site, whereby a needle safety mechanism may be activated for covering the injection needle 6, for example by a distal movement of the sleeve 8.

In the illustrated embodiments the medicament delivery device 1 may be provided with manual needle insertion and manual medicament delivery. Likewise, the medicament delivery device 1 could be provided with automatic needle insertion and/or automatic medicament delivery in order to adjust the injection force.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2, H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

LIST OF REFERENCES 1 medicament delivery device
2 cartridge
2.1 main body section
2.1.1 cartridge shoulder
2.2 neck section
2.2.1 cartridge flange
2.3 cartridge sealing element
3 bung
3.1 bung notch
4 cartridge carrier
4.1 carrier rib
4.2 distal carrier section
4.2.1 carrier collar
4.3 carrier projection
4.4 carrier sealing foil
5 needle cap
5.1 first gap
5.2 second gap
6 injection needle
6.1 outer needle section
6.2 inner needle section
7 piston rod
7.1 rod tip
8 sleeve
D distal direction
L longitudinal axis
P proximal direction
P1 initial position
P2 operating position
x, y, z cartesian coordinates

The invention claimed is:

1. An activating mechanism for a medicament delivery device, comprising:
   a cartridge containing a dosage of a medicament;
   a cartridge carrier configured to hold the cartridge, the cartridge carrier comprising a distal carrier section at a distal end of the cartridge carrier;
   a hollow injection needle arranged within the distal carrier section of the cartridge carrier, the hollow injection needle comprising an inner needle section targeted inside the cartridge carrier, whereby the inner needle section is spaced from the cartridge in a distal direction when the medicament delivery device is in an initial position; and
   a removable needle cap configured to cover and seal an outer needle section of the injection needle that is targeted outside the cartridge carrier,
   wherein the distal carrier section is made from a resilient material so that the distal carrier section is configured to deform radially outwards when the needle cap is removed and the cartridge is moved in the distal direction,
   wherein the distal carrier section comprises a carrier collar that protrudes in a radial inward direction as well as in a radial outward direction,
   wherein the carrier collar is provided to retain the cartridge when the medicament delivery device is in the initial position, and
   wherein a proximal inner surface of the needle cap fits closely to a radial outer surface of the distal carrier section when the medicament delivery device is in the initial position in order to restrict a radial outward deformation of the distal carrier section.

2. The activating mechanism according to claim 1, further comprising a piston rod that is adapted to engage with a bung for displacing the bung within the cartridge.

3. The activating mechanism according to claim 2, wherein the piston rod comprises a rod tip on a distal end of the piston rod, wherein the rod tip is adapted to engage into a correspondingly formed bung notch.

4. The activating mechanism according to claim 3, wherein the piston rod is spaced from a carrier sealing foil in a proximal direction when the medicament delivery device is in the initial position.

5. The activating mechanism according to claim 4, wherein the carrier sealing foil is arranged across an open proximal end of the cartridge carrier.

6. The activating mechanism according to claim 1, wherein an inner diameter of the carrier collar is smaller than a maximum outer diameter of the cartridge, and
   wherein the carrier collar engages with a cartridge shoulder for restricting movement of the cartridge into the distal direction relative to the cartridge carrier when the medicament delivery device is in the initial position.

7. The activating mechanism according to claim 1, wherein a wall thickness of the distal carrier section is reduced compared to a wall thickness of a remaining portion of the cartridge carrier.

8. The activating mechanism according to claim 1, wherein the needle cap comprises a first gap enclosing the outer needle section when the medicament delivery device is in the initial position, and wherein a radial outer surface of a carrier projection that is arranged on the distal carrier section of the cartridge carrier and that protrudes axially in the distal direction is enclosed at least distally by a proximal radial surface of the first gap.

9. An activating mechanism according to claim 1, further comprising a sleeve that is movable along a longitudinal axis relative to the cartridge carrier so as to cover or expose the outer needle section.

10. The activating mechanism of claim 1, wherein the medicament comprises a pharmaceutically active compound.

11. A medicament delivery device comprising:
an activating mechanism comprising:
a cartridge containing a dosage of a medicament;
a cartridge carrier configured to hold the cartridge, the cartridge carrier comprising a distal carrier section at a distal end of the cartridge carrier;
a hollow injection needle arranged within the distal carrier section of the cartridge carrier, the hollow injection needle comprising an inner needle section targeted inside the cartridge carrier, whereby the inner needle section is spaced from the cartridge in a distal direction when the medicament delivery device is in an initial position; and
a removable needle cap configured to cover and seal an outer needle section of the injection needle that is targeted outside the cartridge carrier,
wherein the distal carrier section is made from a resilient material so that the distal carrier section is configured to deform radially outwards when the needle cap is removed and the cartridge is moved in the distal direction,
wherein the distal carrier section comprises a carrier collar that protrudes in a radial inward direction as well as in a radial outward direction,
wherein the carrier collar is provided to retain the cartridge in position as long as the medicament delivery device is in the initial position, and
wherein a proximal inner surface of the needle cap fits closely to a radial outer surface of the distal carrier section when the medicament delivery device is in the initial position in order to restrict a radial outward deformation of the distal carrier section.

12. The medicament delivery device according to claim 11, wherein the cartridge is sealed distally by a cartridge sealing element that is arranged across an open distal end and that is sealed proximally by a bung.

13. The medicament delivery device according to claim 11, wherein the activating mechanism further comprises a piston rod that is adapted to engage with a bung for displacing the bung within the cartridge.

14. The medicament delivery device according to claim 13, wherein the piston rod comprises a rod tip on a distal end of the piston rod, wherein the rod tip is adapted to engage into a correspondingly formed bung notch.

15. The medicament delivery device according to claim 14, wherein the piston rod is spaced from a carrier sealing foil in a proximal direction when the medicament delivery device is in the initial position.

16. The medicament delivery device according to claim 15, wherein the carrier sealing foil is arranged across an open proximal end of the cartridge carrier.

17. The medicament delivery device according to claim 11, wherein an inner diameter of the carrier collar is smaller than a maximum outer diameter of the cartridge, and
wherein the carrier collar engages with a cartridge shoulder for restricting movement of the cartridge into the distal direction relative to the cartridge carrier when the medicament delivery device is in the initial position.

18. The medicament delivery device according to claim 11, wherein a wall thickness of the distal carrier section is reduced compared to a wall thickness of a remaining portion of the cartridge carrier.

19. The medicament delivery device according to claim 11, wherein the needle cap comprises a first gap enclosing the outer needle section when the medicament delivery device is in the initial position, and
wherein a radial outer surface of a carrier projection that is arranged on the distal carrier section of the cartridge carrier and that protrudes axially in the distal direction is enclosed at least distally by a proximal radial surface of the first gap.

20. The medicament delivery device according to claim 11, wherein the activating mechanism further comprises a sleeve that is movable along a longitudinal axis relative to the cartridge carrier so as to cover or expose the outer needle section.

* * * * *